United States Patent [19]
Ebinuma et al.

[11] Patent Number: 5,871,949
[45] Date of Patent: Feb. 16, 1999

[54] METHOD OF QUANTITATIVE ASSAY FOR 1, 5-ANHYDROGLUCITOL AND REAGENT FOR QUANTITATIVE ASSAY

[75] Inventors: Hiroyuki Ebinuma; Koji Ushizawa, both of Ryugasaki, Japan

[73] Assignee: Daiichi Pure Chemicals Co., Ltd., Tokyo, Japan

[21] Appl. No.: 980,792

[22] Filed: Dec. 1, 1997

[30] Foreign Application Priority Data

| Dec. 4, 1996 | [JP] | Japan | 8-323969 |
| Jul. 10, 1997 | [JP] | Japan | 9-200777 |
| Sep. 10, 1997 | [JP] | Japan | 9-262776 |

[51] Int. Cl.$^6$ .............. C12Q 1/32; C12Q 1/54; C12Q 1/00
[52] U.S. Cl. .................. 435/26; 435/14; 435/4
[58] Field of Search .................. 435/26, 14, 4

[56] References Cited

U.S. PATENT DOCUMENTS

| 5,407,806 | 4/1995 | Yabuuchi et al. | 435/26 |
| 5,426,033 | 6/1995 | Kojima et al. | 435/26 |
| 5,468,380 | 11/1995 | Yabuuchi et al. | 435/26 |
| 5,486,458 | 1/1996 | Kojima et al. | 435/14 |

FOREIGN PATENT DOCUMENTS

| 0213279 | 3/1987 | European Pat. Off. . |
| 0261591 | 3/1988 | European Pat. Off. . |
| 0 825258 A | 2/1998 | European Pat. Off. . |
| 1-320998 | 12/1989 | Japan . |
| 02268679 | 11/1990 | Japan . |
| 2-268679 | 11/1990 | Japan . |
| 3-27299 | 2/1991 | Japan . |
| 3-24200 | 4/1991 | Japan . |
| 5-41238 | 6/1993 | Japan . |
| 6-237795 | 8/1994 | Japan . |
| 6-245796 | 9/1994 | Japan . |
| 06303995 | 11/1994 | Japan . |
| 7-71514 | 8/1995 | Japan . |
| 7-102154 | 11/1995 | Japan . |
| 7-108236 | 11/1995 | Japan . |
| 08103295 | 4/1996 | Japan . |
| WO97/31103 | 8/1997 | WIPO . |

OTHER PUBLICATIONS

Kiba N, et al., "Post–column enzyme reactors for chemiluminometric detection of glucose, 1, 5–anhydorglucitol and 3–hydroxybutyrate in an anion–exchange chromatogtographic system", Journal of Chromatography B: Biomedical Applications, vol. 689, No. 2, Feb. 21, 1997, pp. 393–398.

Hayano et al., "Purification and Properties of 3–Ketosucrose–forming Enzyme from the Cells of *Agrobacterium tumefaciens*," *The Journal of Biological Chemistry*, vol. 242, No. 16, pp. 3665–72, Aug. 25, 1967.

Takeuchi et al., "Purification and Properties of Glucoside 3–Dehydrogenase," *The Journal of BioChemistry*, vol. 100, No. 4, pp. 1049–55, May 13, 1986.

Sawada et al., "Proposal for Rejection of *Agrobacterium tumefaciens* and Revised Descriptions for the Genus *Agrobacterium* and for *Agrobacterium radiobacter* and *Agrobacterium rhizogenes*," *International Journal of Systematic Bacteriology*, vol. 43, No. 4, pp.694–702, Oct. 1993.

"Letter to the Editor, Request for a Judicial Opinion Concerning the Type Species of Agrobacterium," *International Journal of Systematic Bacteriology*, vol. 44, No. 2, pp. 373–374, Apr. 1994.

*Primary Examiner*—Louise N. Leary
*Attorney, Agent, or Firm*—Beveridge, DeGrandi, Weilacher & Young, LLP

[57] ABSTRACT

Using a 1,5-anhydroglucitol dehydrogenase capable of acting on 1,5-anhydroglucitol and directly catalyzing a reducing chromophoric agent in the absence of an electron carrier, the 1,5-anhydroglucitol dehydrogenase is allowed to act on 1,5-anhydroglucitol in the presence of the reducing chromophoric agent preferably after the glucose in the specimen has been changed, or while being changed, into such a structure that it does not react with the 1,5-anhydroglucitol dehydrogenase in the specimen, by the aid of a glucose eliminator. Then, the amount of the resultant reduced colored substance is measured. As the 1,5-anhydroglucitol dehydrogenase, an enzyme produced by a microorganism having the ability to produce the 1,5-anhydroglucitol dehydrogenase is preferably used.

12 Claims, 5 Drawing Sheets

OPTIMUM TEMP.

TEMP. STABILITY

METHOD OF QUANTITATIVE ASSAY FOR 1,5-ANHYDROGLUCITOL AND REAGENT FOR QUANTITATIVE ASSAY

FIELD OF THE INVENTION

This invention relates to a method of quantitative assay for 1,5-anhydroglucitol useful for the diagnosis of diabetes and so forth, and to a reagent for such quantitative assay.

BACKGROUND OF THE INVENTION

The 1,5-anhydroglucitol (hereinafter "1,5-AG") is present in body fluids (or humors) such as serum, blood plasma, urine and so forth of humans, and its quantity in the body fluids greatly varies when one suffers from a certain disease, in particular, diabetes. Accordingly, in recent years, it is being an important diagnostic item in clinical diagnosis as a useful diagnostic marker.

As a method of quantitative assay for this 1,5-AG, a method is prevalent in which pyranose oxidase or L-sorbose oxidase is allowed to act on 1,5-AG and the hydrogen peroxide formed is subjected to calorimetric quantitative assay using a color-forming system using peroxidase (see Japanese Patent Publication No. 5-41238). In recent years, this method is applied to general-purpose automatic analyzers. Since, however, these enzymes have a low substrate specificity and may also strongly react with saccharides such as glucose, it has been necessary to beforehand completely remove or eliminate the saccharides in specimens.

Japanese Patent Publication No. 3-24200 also discloses a method in which a 1,5-AG oxidizing enzyme having a high specificity to the 1,5-AG, produced from the genus Pseudomonas sp. NK-85001, is used to quantitatively assay the amount of consumption of oxygen after its reaction with 1,5-AG or the reaction products such as a reduction product of an electron acceptor. However, the method of measuring the amount of consumption of oxygen is not suitable for treating many specimens continuously. The method of measuring the reduction product of an electron acceptor is also not suitable for practical application because the method can not be said to be satisfactory taking account of the reduction product itself which is reversible and unstable and in view of sensitivity, when ferricyanic compounds and dichlorophenolindophenol as disclosed in that publication are used as electron acceptors.

In an instance where the quantitative assay is made using an enzyme such as 1,5-AG dehydrogenase requiring NAD (nicotinamide adenine dinucleotide) as a coenzyme (see Japanese Patent Application Laid-open No. 2-268679), such an enzyme may be affected by enzymes requiring the NAD as a coenzyme, e.g., lactate dehydrogenase and the like, contained in a biological sample, and hence this method has a problem on accuracy.

It is also known that glucoside 3-dehydrogenase [EC 1.1.99.13] confirmed to be present in the soluble fraction of the genus Agrobacterium (The Journal of Biological Chemistry, Vol.242, No.16, pp.3665–3672, 1967) or the membrane fraction of the genus Flavobacterium acts on the 1,5-AG (The Journal of Biochemistry, Vol.100, No.4, pp.1049–1055, 1986). Since, however, these enzymes also have a low substrate specificity, it is necessary to beforehand completely remove or eliminate the saccharides in specimens. Also, they require to use ferricyanic compounds or dichlorophenol indophenol as the electron acceptor, and have problems on safety and sensitivity.

Meanwhile, as the clinical significance of 1,5-AG, in diabetics the 1,5-AG concentration in serum or blood plasma specifically becomes as low as several $\mu g/ml$. On the other hand, with regard to glucose concentration, it is about 100 mg/dl in the case of normal persons, whereas it may reach 1,000 mg/dl in the case of diabetics. Thus, the difference in concentration between 1,5-AG and glucose reaches as much as thousands of times. No enzymes have ever been discovered which enable direct quantitative assay for 1,5-AG and are perfectly specific to it in specimens in which glucose is present together in such a high concentration.

Then, the glucose must be completely removed or eliminated when the quantitative assay is made using the pyranose oxidase or L-sorbose oxidase, having a poor specificity to 1,5-AG and rather strongly reacting with glucose. For this purpose, various methods are proposed. For example, Japanese Patent Publication No. 5-41238 discloses a method in which a pre-treatment operation making use of an ion-exchanged resin is used in combination in order to remove saccharides such as glucose. As a method of eliminating glucose, Japanese Patent Application Laid-open No. 1-320998, Japanese Patent Publication No. 7-71514, Japanese Patent Applications Laid-open No. 6-237795, No. 3-27299, No. 6-245796, etc. disclose a method in which a glucose 6-position phosphorylated enzyme (glucokinase or hexokinase) is used and, also in order to bring this reaction into completion, the equilibrium of the phosphorylation of glucose is intended to be completely directed to glucose 6-phosphate (a coupling system employing several kinds of enzymes and substrates in combination). This method also intends to lessen the inhibitory action of ATP (adenosine 5'-triphosphate) on pyranose oxidase. Another method is also proposed as disclosed in Japanese Patent Publications No. 7-102154 and No. 7-108236, in which pH conditions for allowing pyranose oxidase to act on 1,5-AG are specified or pyranose oxidase with a different origin is used so that the ATP can have no inhibitory action.

However, of the above methods, the method employing an ion-exchanged resin requires so troublesome operations that it is not suitable for treating many specimens. Also, in the method employing a glucose 6-position phosphorylated enzyme and also a coupling system using several kinds of enzymes and substrates in combination, the reaction system is so complicated that the stability of the enzyme, substrate and so forth to be used must be taken into account. The method employing the glucose 6-position phosphorylated enzyme alone also have many restrictions such that the ATP must be used in great excess in order to completely convert and eliminate the glucose and the origin of pyranose oxidase and reaction conditions are limited. Thus, the method can not be so much general-purpose.

SUMMARY OF THE INVENTION

Accordingly, an object of the present invention is to provide a method of quantitative assay for 1,5-AG that can determine the 1,5-AG in specimens by a simple operation in a good precision and at a high sensitivity, and a reagent for such quantitative assay.

To settle the above subject, the present inventors made studies on reaction systems that can be utilized for the analysis of 1,5-AG and made investigations on enzymes that can be utilized therein. As the result, they have discovered that a novel enzyme capable of specifically oxidizing 1,5-AG (hereinafter "1,5-AG dehydrogenase") is present in the membrane fraction of a microorganism belonging to the genus Agrobacterium, that this 1,5-AG dehydrogenase, when allowed to act on 1,5-AG oxidizes the hydroxyl group at the 2-position of 1,5-AG and simultaneously catalyzes the reaction for reducing an electron acceptor such as 2,6-dichlorophenolindophenol, and that, when such reaction is carried out using a reducing chromophoric agent, the hydroxyl group at the 2-position of 1,5-AG can be oxidized even in the absence of electron carriers and simultaneously the reducing chromophoric agent can be directly reduced to produce a colored substance. Thus, based on these findings, they have accomplished the present invention.

More specifically, the method of quantitative assay for 1,5-AG according to the present invention comprises;

allowing a 1,5-AG dehydrogenase to act on 1,5-AG in a specimen in the presence of a reducing chromophoric agent; the 1,5-AG dehydrogenase being capable of acting on 1,5-AG and directly catalyzing the reducing chromophoric agent in the absence of an electron carrier; and measuring the amount of the resultant reduced colored substance.

The reagent for quantitative assay for 1,5-AG according to the present invention comprises;

a 1,5-AG dehydrogenase capable of acting on 1,5-AG and directly catalyzing a reducing chromophoric agent in the absence of an electron carrier; and the reducing chromophoric agent.

According to the present invention, the reducing chromophoric agent is added in a specimen containing 1,5-AG, and the 1,5-AG dehydrogenase is allowed to act on it, whereupon the 1,5-AG dehydrogenase specifically acts on the 1,5-AG to oxidize the 1,5-AG and also directly reduce the reducing chromophoric agent to form a colored substance. The reaction upon which the quantitative assay of this invention is based is shown by the following scheme;

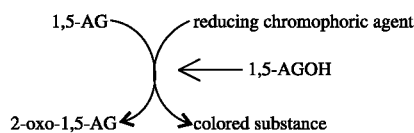

This reaction is an irreversible reaction and is by no means affected by enzymes contained in the biological sample and the like, and hence the quantitative assay can be made at a high sensitivity and accurately. Also, the reaction system is simple and requires only a small number of constituent reagents, and hence the workability can be improved and the method can be applied in automatic analyzers with ease.

DESCRIPTION OF THE PREFERRED EMBODIMENTS

Figure 1:
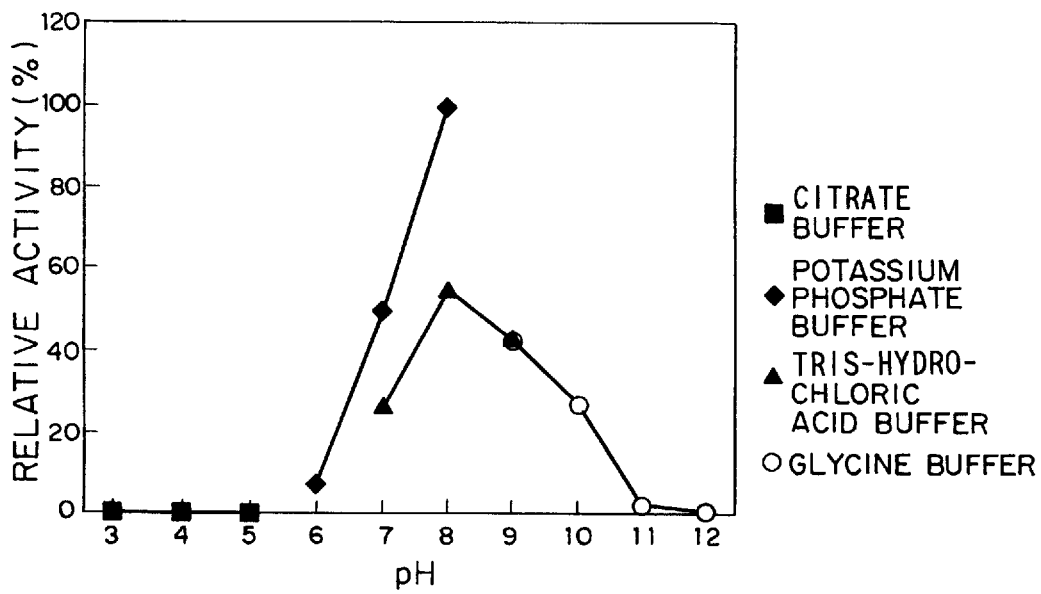
FIG. 1 is a graph showing optimum pH of a 1,5-AG dehydrogenase obtained by culturing *Agrobacterium tumefaciens* NT 1130 strain.

The specimen referred to in the present invention may be any of those intended for measurement of the concentration of 1,5-AG, without any particular limitations, and may include, e.g., serums, blood plasma and urine.

The 1,5-AG dehydrogenase used in the present invention may be any of those capable of specifically acting on the 1,5-AG and simultaneously catalyzing the reaction of directly reducing a reducing chromophoric agent in the absence of an electron carrier, without any particular limitations. Preferably used are those produced from microorganisms belonging to the genus Agrobacterium and having the ability to produce the 1,5-AG dehydrogenase, in particular, those produced from any of *Agrobacterium tumefaciens* IFO 13532, *Agrobacterium tumefaciens* IFO 13533 and *Agrobacterium tumefaciens* NT 1130 strains.

Here, *Agrobacterium tumefaciens* IFO 13532 and *Agrobacterium tumefaciens* IFO 13533 are strains commercially available from Institute for Fermentation, Osaka (IFO), 17-85, Juso-honmachi 2-chome, Yodogawa-ku, Osaka 532, Japan.

The *Agrobacterium tumefaciens* NT 1130 strain is deposited under the deposition number of FERM BP-5997 in National Institute of Bioscience and Human Technology Agency of Industrial Science and Technology, 1-3, Higashi 1-chome, Tsukuba-shi, Ibaraki-ken 305, Japan, according to BUDAPEST TREATY ON THE INTERNATIONAL RECOGNITION OF THE DEPOSIT OF MICROORGANISMS FOR THE PURPOSES OF PATENT PROCEDURE. The depositor is Daiichi Pure Chemicals Co., Ltd., 1-5, Nihonbashi 3-chome, Chuo-ku, Tokyo 103, Japan.

Of these, the *Agrobacterium tumefaciens* NT 1130 strain, isolated from the soil by the present inventors, which is particularly preferred because of its superior storage stability compared with the existing strains *Agrobacterium tumefaciens* IFO 13532 and *Agrobacterium tumefaciens* IFO 13533. Of course, the microorganisms not only may be selected from the deposited strains but also may be further isolated from nature such as soils, or mutant strains may also be used. Also, among these strains, any genes participating to the production of enzymes isolated from these strains may be incorporated into hosts to effect enzyme production.

For reference, micological properties of the *Agrobacterium tumefaciens* NT 1130 are given below.

A. Morphological Features
1) Shape and size of cell: Rod-shaped bacteria with a size of 0.3–0.5×1.0–3.0
2) Presence or absence of pores: not recognized
3) Motility: It possesses peripheral flagella with motility.
4) Gram staining: negative B. Physiological Properties
1) Catalase: positive
2) Oxidase: positive
3) Urease: positive
4) Gelatin liquefaction: negative
5) Indole formation: negative
6) Formation of hydrogen sulfide; negative
7) Utilization of citric acid: negative
8) Aesculin decomposability: positive
9) β-galactosidase: positive
10) Reduction of nitrate: positive (+)
11) Behavior to oxygen: aerobic
12) Growth temperature: 25° to 30° C.
11) Behavior to saccharides: It forms acids from glucose, xylose, mannose, arabinose, fructose, maltose, rhamnose, mannitol and saccharose, and generates no gas.

C. Quinone Compositional Analysis Ubiquinone-10 (98%)

Based on the foregoing results, this strain is considered to be grouped in the genus Agrobacterium. Usually, in the identification of a microorganism, its properties are compared with the classification in "Bergey's Manual of Determinative Bacteriology", where taxonomical properties of microorganisms are compiled, to make identification of the microorganism. With regard to the genus Agrobacterium to which the present strain is considered to belong, a systemic classification according to gene sequence of 16SrRNA is recently attempted (see International Journal of Bacteriology, Vol.43, 1993, pp.694–702 and Vol.44, No.2, 1994, pp.373–374), based on the results of which the standard of classification has been changed and re-drawn up. As the result, unification of species and changes of classification of strains have been added to become no longer adjustable to the "Bergey's Manual of Determinative Bacteriology".

Accordingly, a systemic classification according to gene sequence of 16SrRNA was also attempted also in respect of the present strain. As a method therefor, the entire gene sequence of 16SrRNA of the present strain was determined, and its homology to the gene sequences of microorganisms registered and laid open in the data base (GenBank, EMBL and DDBJ) of genes was searched. As the result, the present strain was found homologous by 99.4% to *Agrobacterium tumefaciens*. Based on this result, the present strain was identified to be a bacterium belonging to the genus Agrobacterium and the species *tumefaciens*, and the present strain was named *Agrobacterium tumefaciens* NT 1130. The present strain is, as previously stated, deposited in National Institute of Bioscience and Human Technology Agency of Industrial Science and Technology (1-3, Higashi 1-chome, Tsukuba-shi, Ibaraki-ken, Japan), which was deposited on Jun. 27, 1997 under the deposition number of FERM BP-5997.

The 1,5-AG dehydrogenase used in the present invention can be produced by, e.g., culturing the strain in a nutrient broth so as to form and accumulate 1,5-AG dehydrogenase in the membrane fraction, and collecting it. As the nutrient broth, a medium containing a carbon source, an inorganic nitrogen source and an inorganic salt may be used. As the carbon source, saccharides may be used basically which can enzymatically induce L-sorbose, glucose and so forth. As the inorganic nitrogen source, ammonium sulfate, ammonium chloride, ammonium phosphate and so forth may be used, and as the inorganic salt, salts of sodium, potassium, magnesium, iron, manganese and so forth.

The strain may preferably be cultured under aerobic conditions by, e.g., shaking or aerial agitation, and preferably at pH 6 to pH 8 and at 25° C. to 35° C. The culture is completed in 1 to 7 days, and usually 2 to 4 days. As a result of culture thus performed, the 1,5-AG dehydrogenase is formed and accumulated mainly in the membrane fraction of cells.

After the culture, to harvest the enzyme of the present invention from the microorganism, the cells are destroyed using a dyno mill or by ultrasonic wave treatment in a suitable buffer solution, and the membrane fraction is separated from the treated solution by centrifugation or the like. Subsequently, the enzyme is solubilized from the membrane fraction by using a nonionic detergent or surface-active agent such as Triton X-100, and the insoluble matter is removed by centrifugation to obtain an extract containing the 1,5-AG dehydrogenase. A purified enzyme is obtained by subjecting this extract to any of hydrophobic chromatography, ion-exchange chromatography, hydroxyapatite purification, gel filtration and so forth, which are techniques commonly used in the purification of enzymes and may be used in appropriate combination.

The 1,5-AG dehydrogenase obtained from the *Agrobacterium tumefaciens* NT 1130 strain in the manner as described above exhibits physicochemical properties as shown below.

The activity of the 1,5-AG dehydrogenase is measured in the following way. That is, 3.0 ml in total of an enzyme-containing solution comprised of 1.5 ml of 0.2M potassium phosphate buffer (pH 8.0), 0.3 ml of 0.25% by weight nitrotetrazolium blue, 0.3 ml of 2% by weight nonionic surface-active agent, 0.3 ml of an aqueous 50 mM 1,5-AG solution, 0.45 ml of water and 0.15 ml of an enzyme solution is reacted at 37° C., and a change in absorbance (ΔmOD/min) at 540 nm is measured. The molecular extinction coefficient (or molar absorption coefficient) of a formazan dye formed under such conditions is given as $16.7 \times 10^3$ and the quantity of the enzyme capable of forming 1 μmol of formazan in one minute is regarded as one unit, where the activity of the 1,5-AG dehydrogenase is determined according to the following expression;

Enzymatic activity (units/ml) =

$$\frac{\Delta mOD/min}{16.7 \times 10^3} \times \frac{3.0}{0.15} \times \text{dilution of enzyme}$$

(1) Activity:

The enzyme of the present invention is added in 100 mM of a tris-hydrochloric acid buffer (pH 9.0) containing 1 mM of 2,6-dichlorophenolindophenol and 2.5 mM of 1,5-AG, and reaction was carried out at 37° C. The molar balance between the reaction product in the reaction mixture and the reaction was analyzed with time by high-speed liquid chromatography (HPLC) under conditions shown in Table 1.

TABLE 1

| HPLC analysis conditions | |
|---|---|
| Column: | Shodex SUGAR SH1011 |
| Eluent: | Water |
| Column temp. | 30° C. |

TABLE 1-continued

HPLC analysis conditions

| | |
|---|---|
| Flow rate: | 0.75 ml/min |
| Detector: | Differential refractometer (RI) |

As the result, the peak of 1,5-AG at a retention time of 10.0 minutes decreased with the progress of the reaction, an a peak of the reaction product anew appeared at the position of a retention time of 9.6 minutes. The molar balance of this reaction was in agreement. Glucosido-3-dehydrogenase (EC1.1.99.13) having the action to oxidize the hydroxyl group at the 3-position of 1,5-AG was also reacted under the same conditions as the above to make analysis by HPLC. As the result, with a decrease in peak of 1,5-AG, a peak of the reaction product anew appeared at the position of a retention time of 10.8 minutes. Meanwhile, pyranose oxidase (EC1.1.3.10) having the action to oxidize the hydroxyl group at the 2-position of 1,5-AG was added in 40 mM boric acid buffer (pH 7.5) containing 2.5 mM of 1,5-AG, and reaction was carried out at 37° C. As the result, with a decrease in peak of 1,5-AG, a peak of the reaction product anew appeared at the position of a retention time of 9.6 minutes. From the agreement in retention time in these results between the reaction product obtained when the present enzyme was allowed to act on 1,5-AG and the reaction product obtained when the pyranose oxidase was allowed to act on 1,5-AG, it is seen that the moiety where the 1,5-AG is oxidized by the present enzyme is the hydroxyl group at the 2-position.

(2) Substrate specificity:

Relative activities (substrate specificity) of instances where the 1,5-AG was replaced with various sugar solutions (all having a final concentration of 5 mM) in the above method of measuring the enzymatic activity are shown in Table 2. The present enzyme strongly acted on 1,5-AG, weakly acted on L-sorbose and slightly acted on D-glucose.

TABLE 2

| Substrate | Relative activity |
|---|---|
| 1,5-AG | 100 |
| L-sorbose | 25 |
| D-glucose | 11 |
| D-galactose | 0 |
| D-fructose | 2 |
| Glucitol | 0 |
| Myoinocitol | 0 |
| Maltose | 0 |

(3) Optimum pH:

Using the present enzyme, enzymatic activities were measured in instances where the buffer in the above method of measuring the enzymatic activity was replaced with a citric acid buffer, a potassium phosphate buffer, a tris-hydrochloric acid buffer and a glycine buffer, having various pH values.

Results obtained are shown in FIG. 1. As can be seen from FIG. 1, the present enzyme has an optimum pH at about 8.0 to 9.0.

(4) pH stability:

The present enzyme was added in each of the citric acid buffer, the potassium phosphate buffer, the tris-hydrochloric acid buffer and the glycine buffer (each buffer, 200 mM), having various pH values, and treated at 37° C. for 60 minutes. Thereafter, the residual enzymatic activities were measured.

Figure 2:
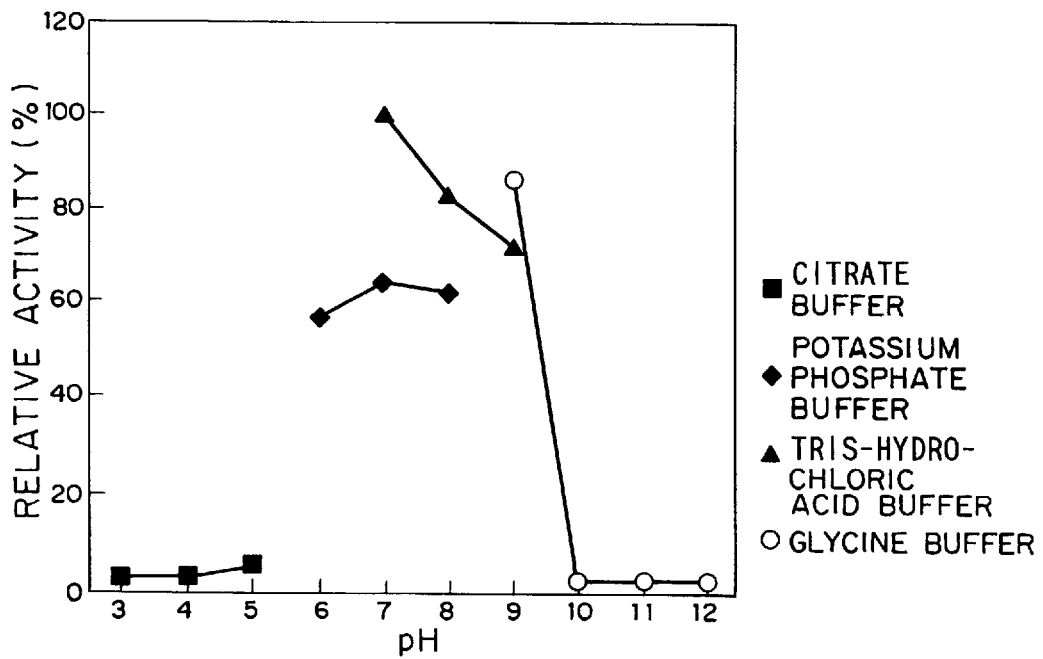
FIG. 2 is a graph showing pH stability of the above 1,5-AG dehydrogenase.

Results obtained are shown in FIG. 2. As can be seen from FIG. 2, the present enzyme has a stable pH in the range of from 6.0 to 9.0.

(5) Optimum temperature:

Using the present enzyme, reaction was carried out at various temperatures under the composition as in the above method of measuring the enzymatic activity.

Figure 3:
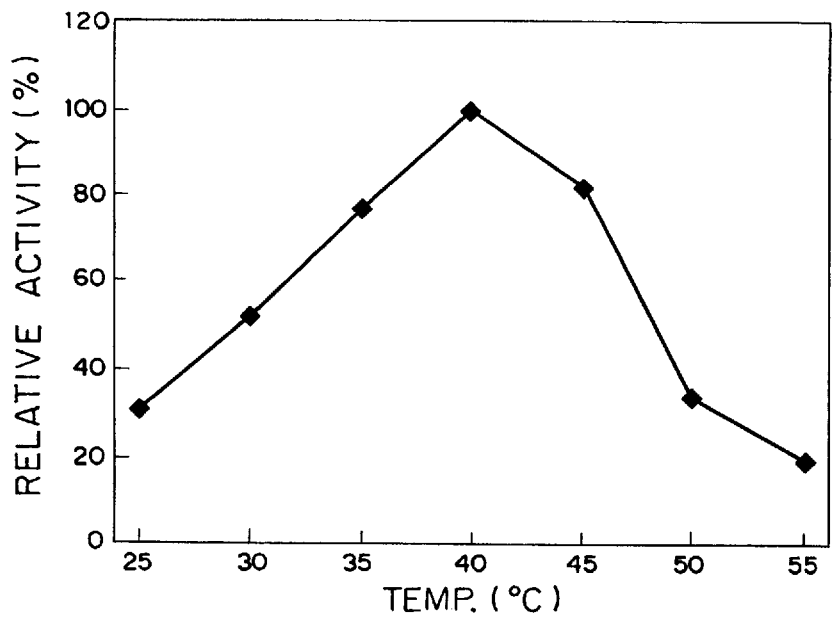
FIG. 3 is a graph showing optimum temperature of the above 1,5-AG dehydrogenase.

Results obtained are shown in FIG. 3. As can be seen from FIG. 3, the present enzyme has an optimum temperature at about 35 to 45° C.

(6) Temperature stability:

The present enzyme was added in 20 mM of the potassium phosphate buffer, and treated at various temperatures for 10 minutes. Thereafter, the residual enzymatic activities were measured.

Figure 4:
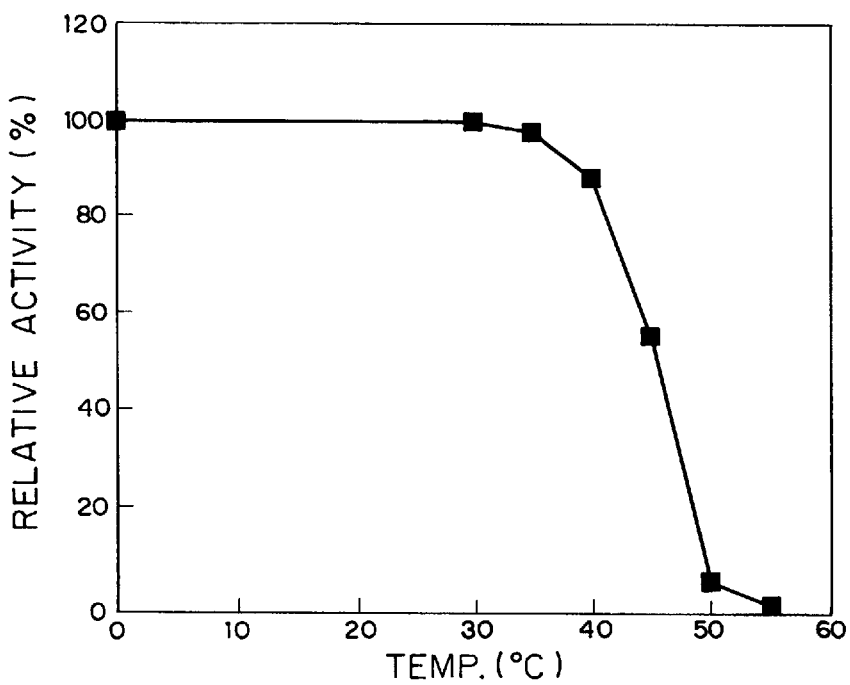
FIG. 4 is a graph showing temperature stability of the above 1,5-AG dehydrogenase.

Results obtained are shown in FIG. 4. As can be seen from FIG. 4, the present enzyme is stable up to about 40° C. by 90% or more.

(7) Electron acceptor:

In 100 mM of the potassium phosphate buffer (pH 8.0), various electron acceptors were made present together with the present enzyme, where the activities on the respective electron acceptors were indicated as relative activities, which were as shown in Table 3.

As can be seen from Table 3, besides the reducing chromophoric agent nitrotetrazolium blue, 2,6-dichlorophenolindophenol and a ferricyanide compound are utilizable.

TABLE 3

| Electron acceptor | Final purity (mM) | Relative activity (%) |
|---|---|---|
| 2,6-Dichlorophenolindophenol | 0.1 | 100 |
| Potassium ferricyanide | 10.1 | 67 |
| Cytochrome | 0.1 | 0 |
| NAD | 1.0 | 0 |
| NADP | 1.0 | 0 |
| Oxygen | dissolved oxygen | 0 |
| Nitrotetrazolium blue | 1.0 | 53 |

(8) Molecular weight:

The present enzyme had a molecular weight of about 55,000 as determined by sodium dodecyl sulfate polyacrylamide electrophoresis.

(9) Km Value;

The Km value of the present enzyme with respect to 1,5-AG was determined by the Lineweaver-Burk plot to reveal that it was about 0.5 mM.

(10) Storage stability:

In 100 mM of the tris-hydrochloric acid buffer (pH 7.0), the present enzyme was dissolved in a concentration of 0.1 u/ml, and the resultant solution was stored under conditions of 4° C. for 14 days. After storage for 7 days and 14 days, its residual activity was measured to obtain the results as shown in FIG. 5.

Figure 5:
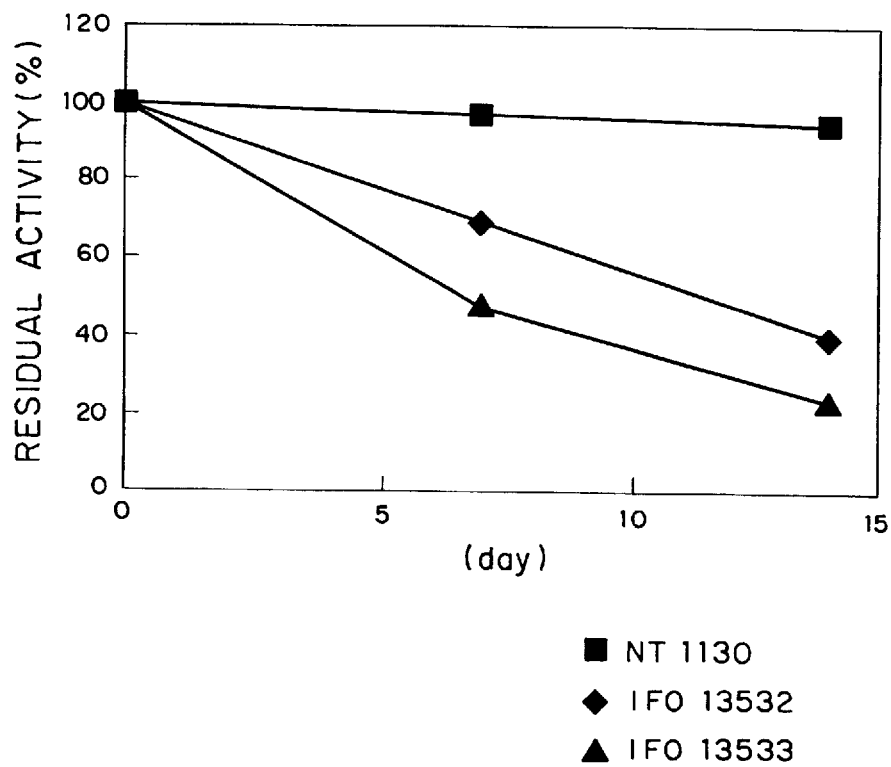
FIG. 5 is a graph showing comparison of storage stability between the above 1,5-AG dehydrogenase, a 1,5-AG dehydrogenase derived from *Agrobacterium tumefaciens* IFO 13532 and a 1,5-AG dehydrogenase derived from *Agrobacterium tumefaciens* IFO 13533.

Meanwhile, for comparison, 1,5-AG dehydrogenases prepared in the same manner as the above but using the known strains *Agrobacterium tumefaciens* IFO 13532 and *Agrobacterium tumefaciens* IFO 13533, deposited in and releasable from the Institute for Fermentation, Osaka (IFO), and the storage stability was measured in the same manner as the above to obtain the results shown together in FIG. 5.

In FIG. 5, the line with solid quadrangles denotes the results of the present enzyme derived from *Agrobacterium tumefaciens* NT 1130 strain; the line with solid lozenges, the results of the enzyme derived from *Agrobacterium tumefa-*

*ciens* IFO 13532; and the line with solid triangles, the results of the enzyme derived from *Agrobacterium tumefaciens* IFO 13533.

As shown in FIG. 5, the 1,5-AG dehydrogenase derived from *Agrobacterium tumefaciens* NT 1130 strain has a residual activity of 90% or more after storage for 14 days, showing a good storage stability. On the other hand, the 1,5-AG dehydrogenase derived from *Agrobacterium tumefaciens* IFO 13532 and the 1,5-AG dehydrogenase derived from *Agrobacterium tumefaciens* IFO 13533 both had a residual activity of 40% or less after storage for 14 days, showing an inferior storage stability.

The 1,5-AG dehydrogenase derived from the Agrobacterium tumefaciens NT 1130 strain discovered by the present inventors showed a remarkable difference in the above storage stability but did not show a meaningful difference in other physicochemical properties, compared with the 1,5-AG dehydrogenase derived from *Agrobacterium tumefaciens* IFO 13532 and the 1,5-AG dehydrogenase derived from *Agrobacterium tumefaciens* IFO 13533.

The quantitative assay for 1,5-AG can be carried out by, e.g., the following method: The specimen is incubated together with 1,5-AG dehydrogenase or an enzyme preparation containing it, in the presence of the reducing chromophoric agent to form a reduced colored substance, and the amount of the colored substance thus formed is measured, thus the 1,5-AG in the specimen can be quantitatively assayed.

As a buffer usable in the above quantitative assay, any of those usually used may be used, such as phosphoric acid buffers, tris-hydrochloric acid buffers, Good's buffers and boric acid buffers, having a pH of 6 to 10.

As the reducing chromophoric agent, tetrazolium compounds or salts thereof may be used. Stated specifically, tetrazolium blue (hereinafter "NTB), 2-(4-iodophenyl)-3-(4-nitrophenyl)-5-phenyl-2H tetrazolium chloride, 3-(4,5-dimethyl-2-thiazolyl)-2,5-diphenyl-2H tetrazolium bromide, 2-(4-iodophenyl)-3-(4-nitrophenyl)-5-(2,4-disulfophenyl-2H tetrazolium salts (hereinafter "WST1"), etc. may be used, and may preferably be used in a concentration ranging from 50 to 2,000 μmol/liter, and particularly from 100 to 1,000 μmol/liter.

In the method of quantitative assay according to the present invention, the 1,5-AG dehydrogenase may preferably be used in the range of from 20 to 10,000 units/liter, and particularly from 200 to 2,000 μmol/liter.

Amount of the reduced colored substance present in the reaction mixture can be determined, after the reaction carried out as described above, by measuring changes in absorbance after a certain time or absorbance within a certain time, at absorption wavelength specific to the colored substance.

In the method of quantitative assay according to the present invention, the 1,5-AG dehydrogenase may preferably be allowed to act on the 1,5-AG present in the specimen, in the presence of the reducing chromophoric agent after the glucose in the specimen has been changed, or while being changed, into such a form that the 1,5-AG dehydrogenase does not act thereon. Accordingly, it is preferable to incorporate a glucose eliminator in the reagent. As this glucose eliminator, those containing a glucose 6-position phosphorylated enzyme and an adenosine triphosphate may preferably be used.

The 1,5-AG dehydrogenase used in the present invention has a high specificity to 1,5-AG, but not a perfect specificity, and is seen to slightly act on glucose. Hence, it follows that it is reasonably affected by the glucose when the 1,5-AG is assayed which is present in diabetes patiants' serums or blood plasma in which the difference in concentration between 1,5-AG and glucose reaches as much as thousands of times. Accordingly, the glucose eliminator may be used in combination so that the accuracy of assay can be more improved when such diabetes patiants' serums, blood plasma and the like are used as the specimen.

In such an instance, in the present invention, the glucose present together in the specimen may be decreased to only a certain extent, whereby the influence of glucose can be made to an almost negligible level because of the enzyme's high specificity to 1,5-AG, thus it is unnecessary to completely eliminate the glucose. Accordingly, as the glucose eliminator, it is enough to use such a simple agent that may decrease the glucose to a concentration level where it no longer reacts with the 1,5-AG dehydrogenase.

The glucose 6-position phosphorylated enzyme used as the glucose eliminator may include glucokinase and hexokinase, and commercially available ones may be used without any particular limitations so long as they are classified as EC2.7.1.2 or EC2.7.1.1. Preferably, a glucokinase having a high specificity to glucose may be used. Any of these may be used in an amount of approximately from 0.1 to 50 U/ml, which may vary depending on the amount of glucose in the specimen. As for the adenosine triphosphate (ATP), necessary for the phosphorylation of glucose, it may be used in an amount of approximately from 1 to 20 mM, which may vary depending on the amount of glucose in the specimen. Usually, as an agent for accelerating the glucose phosphorylation reaction, magnesium ions are further incorporated as an inorganic or organic salt in an amount of from 5 to 50 mM. The phosphorylation reaction for eliminating glucose is carried out in a buffer with pH 6 to 10 at 20° to 50° C., and preferably 25° to 37° C., for about 10 minutes immediately after the addition. As usable buffers, any of those usually used may be used, such as glycine buffers, tris-hydrochloric acid buffers and Good's buffers.

The treatment to eliminate glucose in the specimen by the use of the above reagents may preferably be made in the form of pretreatment of the reaction of the 1,5-AG dehydrogenase. Since, however, the 1,5-AG dehydrogenase used in the present invention has so high a substrate specificity that it is enough for the glucose to be decreased to a concentration level where it no longer reacts with the 1,5-AG dehydrogenase. Thus, it is also possible to carry out in one-shot reagent the treatment of glucose and the quantitative assay of 1,5-AG in the above reagents while making combination of the glucose eliminator, amount of 1,5-AG dehydrogenase and reaction time under appropriate conditions.

Accordingly, the quantitative assay can be made using the reagent for 1,5-AG quantitative assay of the present invention separately in combination with the glucose eliminator or the enzyme for quantitative assay, or using a mixture of the glucose eliminator and the enzyme for quantitative assay as one-shot reagent. Stated more specifically, the reagent may preferably be constituted of two reagents, a first reagent containing the reducing chromophoric agent and glucose eliminator and a second reagent containing the 1,5-AG dehydrogenase, or constituted of one-shot reagent containing all the reducing chromophoric agent, the glucose eliminator and the 1,5-AG dehydrogenase.

EXAMPLES

The present invention will be described below in greater detail by giving Examples. The present invention is by no means limited to these.

Production Example 1

(Preparation of solubilized membrane fraction having 1,5-AG activity, derived from Agrobacterium tumefaciens NT 1130 strain)

50 ml of a medium (pH 7.0) comprising 2% of dipotassium phosphate, 0.5% of monopotassium phosphate, 0.75% of potassium chloride, 2.5% of sodium chloride, 1.25% of ammonium chloride, 0.025% of sodium sulfate, 0.005% of magnesium sulfate and 0.1% of L-sorbose was added in a culture flask of 200 ml in volume, which were then disinfected at 120° C. for 15 minutes, followed by cooling. To the medium thus treated, one platinum loop of Agrobacterium tumefaciens NT 1130 strain (FERM BP-5997) was inoculated to carry out shaking culture at 30° C. for 3 days to prepare a seed culture solution. In a 2 liter culture flask, 10 ml of the seed culture solution thus obtained was inoculated in 1,000 ml of a liquid medium having the same composition as the above to carry out shaking culture at 30° C. for 3 days.

After the culture was completed, cells were collected by centrifugation. The cells obtained were in an amount of about 2 g per liter of the culture solution. The cells thus obtained were suspended in 2.5 ml per gram of a 20 mM potassium phosphate buffer, and the cells were disrupted by means of an ultrasonic oscillator. The broken solution obtained was centrifuged at 10,000×g to remove intact cells and cell debris, and the resultant supernatant was further centrifuged at 100,000×g to obtain the membrane fraction. The fraction was suspended in a 20 mM potassium phosphate buffer (pH 7.2) containing 10 ml of 1% Triton X-100 to solubilize the enzyme from the membrane fraction overnight with stirring. The solubilized solution thus obtained was again centrifuged at 100,000×g to remove membrane residues, to obtain a crude enzyme solution. The enzymatic activity of this crude enzyme was determined by the measuring method previously described. As a result, an activity of 2 units per gram of cells was obtained.

Production Example 2

(Purification of 1,5-AG dehydrogenase)

The solubilized solution obtained in Production Example 1 was passed through a hydroxyapatite column previously equilibrated with a 20 mM potassium phosphate buffer (pH 7.2) containing 10 ml of 1% Triton X-100, to apply the enzyme to the column, which was then-washed with a buffer having the same composition, followed by elution in a linear gradient by the use of the 20 mM potassium phosphate buffer (pH 7.2) containing 10 ml of 1% Triton X-100 to collect active fractions of the enzyme. In order to more enhance its specific activity, the eluate was again passed through the hydroxyapatite column to repeat the above procedure, and the active fractions were collected, followed by ultrafiltration to effect concentration, thus a purified enzyme was obtained as a protein having a specific activity of 14 units/mg. This purified sample showed a single protein band in polyacrylamide electrophoresis.

Example 1

(Quantitative assay of 1,5-AG in a reagent system making use of no glucose eliminator)

Using WST-1 as the reducing chromophoric agent and the 1,5-AG dehydrogenase obtained in Production Example 2, a quantitative assay reagent comprising the first reagent and second reagent as shown in Table 4 was prepared. Using this reagent, 1,5-AG solutions with various concentrations and glucose solutions with various concentrations were put to measurement.

More specifically, to 10 µl each of solutions containing 1,5-AG in various concentrations or solutions containing 1,5-AG in a constant concentration and to which glucose was added in different concentrations, 320 µl of the first reagent shown in Table 4 was added to carry out reaction at 37° C. for 5 minutes, and subsequently 70 µl of the second reagent was added to similarly carry out reaction at 37° C. for 5 minutes. Thereafter, using a Hitachi 707 type automatic analyzer, absorbance was measured in two-point end assay at 450 nm as principal wavelength and 700 nm as secondary wavelength.

Figure 6:
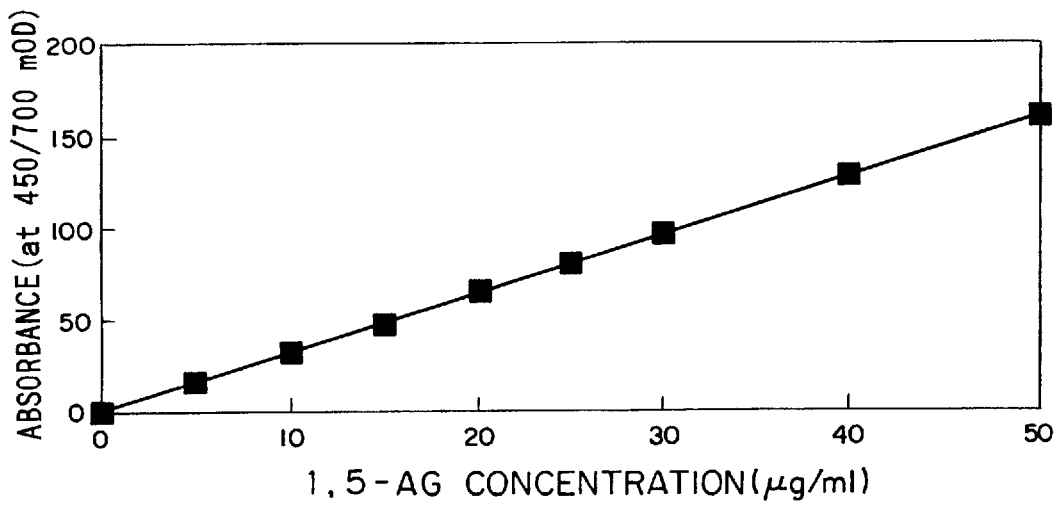
FIG. 6 is a graph showing results of the measurement of absorbance of 1,5-AG solutions with various concentrations, using a first reagent containing the reducing chromophoric agent and a second reagent containing the 1,5-AG dehydrogenase.
Figure 7:
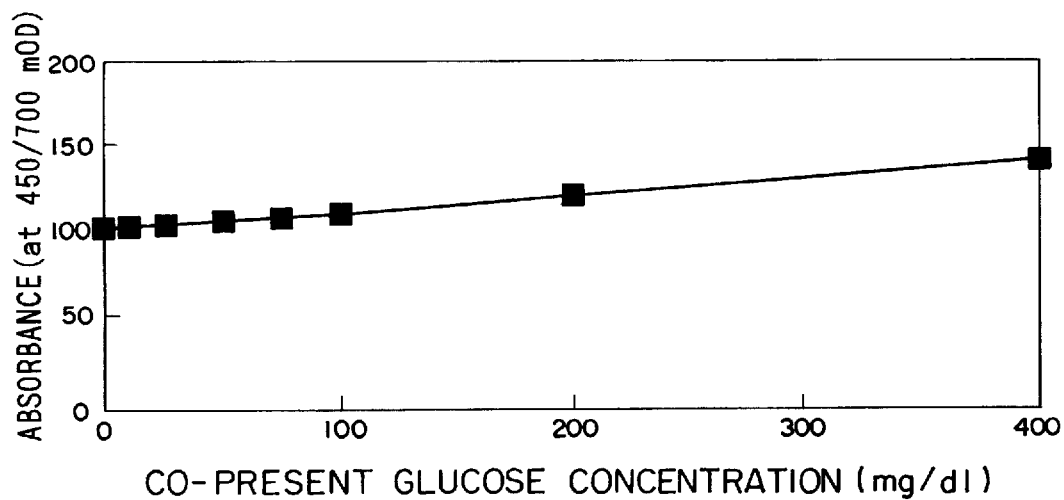
FIG. 7 is a graph showing results of the measurement of absorbance of solutions containing 1,5-AG in a constant concentration and to which glucose is added in various concentrations, using a first reagent containing the reducing chromophoric agent and a second reagent containing the 1,5-AG dehydrogenase.

The results of measurement are shown in FIGS. 6 and 7. FIG. 6 shows results of measurement made on solutions containing 1,5-AG in various concentrations, and FIG. 7 shows results of measurement made on solutions containing 1,5-AG in a constant concentration and containing glucose in various concentrations.

As can be seen from FIG. 6, a linear chromophoric absorbance is obtained at the 1,5-AG concentration of from 0 to up to 50 µg/ml and the quantitative assay of 1,5-AG is possible. As also can be seen from FIG. 7, when glucose is present together, the absorbance increases with an increase in the glucose concentration, but the change in absorbance is small when the glucose is present together in a concentration of about 100 µl/ml, and the change is less than 2 µg/ml in terms of 1,5-AG. Thus, as can be seen from these results, the use of the 1,5-AG dehydrogenase having a high substrate specificity, obtained in Production Example 2, enables substantially accurate assay of the 1,5-AG even if the glucose remains at the level of 1,5-AG concentration. This even means that it is unnecessary to take the trouble of completely eliminating the glucose.

TABLE 4

| First reagent | Second reagent |
| --- | --- |
| Glycine buffer: 100 mM | Phosphate buffer: 50 mM |
| WST-1: 1.25 mM | 1,5-AG dehydrogenase: 5 U/ml |
| Triton X-100: 0.1% | Triton X-100: 0.1% |
| (pH 9.0) | (pH 7.0) |

Example 2

(Quantitative assay of 1,5-AG in a reagent system making use of glucose eliminator in combination)

Using first and second reagents having the composition shown in Table 5, the first reagent containing a glucose eliminator and the second reagent containing the 1,5-AG dehydrogenase obtained in Production Example 2, solutions containing 1,5-AG in a constant concentration and to which glucose was added in different concentrations were prepared. Using the solutions as samples, the procedure of Example 1 was repeated to make quantitative assay of 1,5-AG. Results obtained are shown in FIG. 8.

Figure 8:
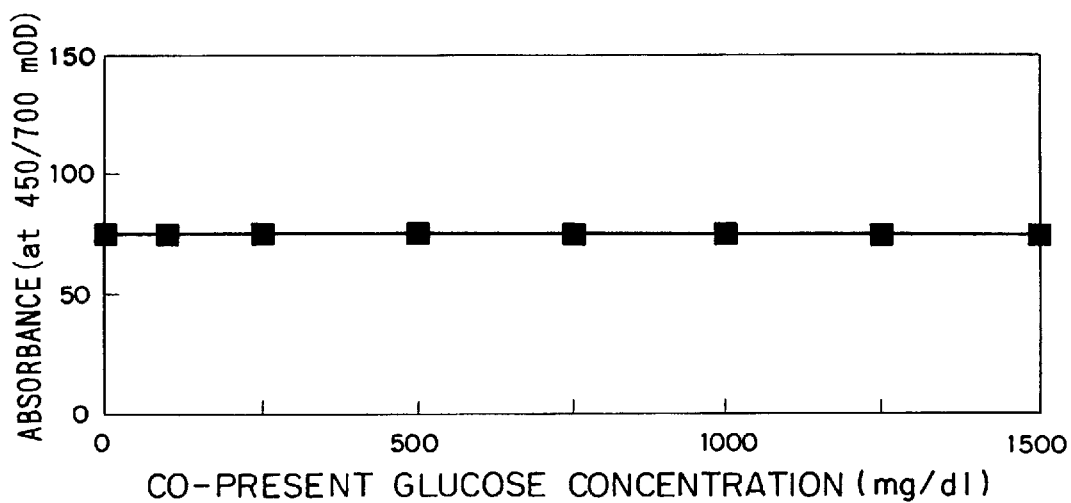
FIG. 8 is a graph showing results of the measurement of absorbance of solutions containing 1,5-AG in a constant concentration and to which glucose is added in various concentrations, using a first reagent containing the reducing chromophoric agent and a glucose eliminating agent and a second reagent containing the 1,5-AG dehydrogenase.

As shown in FIG. 8, the sample containing 1,500 mg/dl of glucose has the same absorbance as the sample containing no glucose. As can be seen therefrom, the quantitative assay of 1,5-AG can be accurately made only by roughly eliminating the high-concentration glucose by a simple elimination method.

TABLE 5

| First reagent | Second reagent |
| --- | --- |
| Glycine buffer: 100 mM | Phosphate buffer: 50 mM |
| WST-1: 1.25 mM | 1,5-AG dehydrogenase: 5 U/ml |

TABLE 5-continued

| First reagent | Second reagent |
| --- | --- |
| Triton X-100: 0.1% | Triton X-100: 0.1% |
| Glucokinase: 3 U/ml | |
| ATP: 10 mM | (pH 7.0) |
| Magnesium acetate: 5 mM | |
| (pH 9.0) | |

Example 3

(Quantitative assay of 1,5-AG in one-shot reagent system containing glucose eliminator)

Using a one-liquid reagent having the composition shown in Table 6, containing a glucose eliminator, a reducing chromophoric agent and the 1,5-AG dehydrogenase obtained in Production Example 2, solutions containing 1,5-AG in a constant concentration and to which glucose was added in different concentrations were prepared. Using the solutions as samples, the quantitative assay of 1,5-AG was made.

More specifically, to 8 μl each of the samples, 312 μl of the reagent shown in Table 6 was added to carry out reaction for 15 minutes. Thereafter, using a Hitachi 707 type automatic analyzer, absorbance was measured in two-point end assay at 450 nm as principal wavelength and 700 nm as secondary wavelength. Results obtained are shown in FIG. 9.

Figure 9:
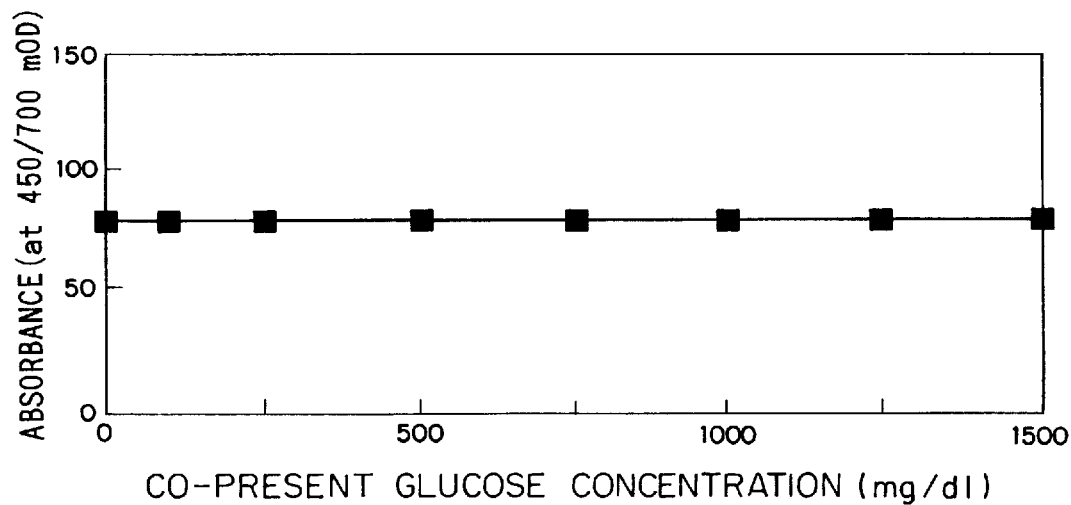
FIG. 9 is a graph showing results of the measurement of absorbance of solutions containing 1,5-AG in a constant concentration and to which glucose is added in various concentrations, using a reagent containing the reducing chromophoric agent, the glucose eliminating agent and the 1,5-AG dehydrogenase in one-shot reagent.

As can be seen from FIG. 9, the sample containing 1,500 mg/dl of glucose has the same absorbance as the sample containing no glucose, and it is seen therefrom that the quantitative assay of 1,5-AG can be accurately made using one-shot reagent even in samples containing glucose in a high concentration.

TABLE 6

| Reagent | |
| --- | --- |
| Glycine buffer: | 100 mM |
| WST-1: | 1 mM |
| Triton X-100: | 0.1% |
| Glucokinase: | 12 U/ml |
| ATP: | 10 mM |
| Magnesium acetate: | 5 mM |
| 1,5-AG dehydrogenase: | 0.4 U/ml |
| (pH 9.0) | |

As described above, according to the present invention, the reducing chromophoric agent is added in the specimen containing 1,5-AG, and the 1,5-AG dehydrogenase is allowed to act on it, whereupon the 1,5-AG dehydrogenase specifically acts on the 1,5-AG to oxidize the 1,5-AG and simultaneously directly reduce the reducing chromophoric agent to form color. Since this reaction is an irreversible reaction and is by no means affected by enzymes contained in the biological sample and the like, the quantitative assay can be made at a high sensitivity and accurately. Also, since the reaction system is simple and requires only a small number of constituent reagents, the operability can be improved and the method can be applied in automatic analyzers with ease.

When the glucose eliminator is used in combination so that the glucose present together in the specimen is decreased to a certain extent, the influence of glucose can be made to an almost negligible level because of the enzyme's high specificity to 1,5-AG. Hence, a high assay precision can be attained even when the diabetes patiants' serums or blood plasma in which the difference in concentration between 1,5-AG and glucose reaches as much as thousands of times are used as the specimen.

What is claimed is:

1. A method of quantitative assay for 1,5-anhydroglucitol, comprising;

allowing a 1,5-anhydroglucitol dehydrogenase to act on 1,5-anhydroglucitol in a specimen in the presence of a reducing chromophoric agent; said 1,5-anhydroglucitol dehydrogenase being capable of acting on 1,5-anhydroglucitol and directly catalyzing the reducing chromophoric agent in the absence of an electron carrier; and measuring the amount of the resultant reduced colored substance.

2. The method according to claim 1, wherein said 1,5-anhydroglucitol dehydrogenase is allowed to act on said 1,5-anhydroglucitol present in the specimen, in the presence of the reducing chromophoric agent after the glucose in the specimen has been changed, or while being changed, into such a form that it does not react with said 1,5-anhydroglucitol dehydrogenase in the specimen, by the aid of a glucose eliminator.

3. The method according to claim 2, wherein said glucose eliminator contains a glucose 6-position phosphorylated enzyme and an adenosine triphosphate.

4. The method according to claim 1, wherein said reducing chromophoric agent is a tetrazolium compound or a salt thereof.

5. The method according to claim 1, wherein said 1,5-anhydroglucitol dehydrogenase is an enzyme produced by a microorganism belonging to the genus Agrobacterium and having the ability to produce the 1,5-anhydroglucitol dehydrogenase.

6. The method according to claim 1, wherein said 1,5-anhydroglucitol dehydrogenase is an enzyme having the following physicochemical properties.

(1) Activity:
  in the absence of electron carriers, said dehydrogenase specifically acts on 1,5-anhydroglucitol to oxidize its hydroxyl group at the 2-position and catalyzes the reaction of directly reducing the reducing chromophoric agent;

(2) Substrate specificity:
  said dehydrogenase strongly acts on 1,5-anhydroglucitol and weakly acts on L-sorbose and said dehydrogenase also slightly acts on D-glucose;

(3) Optimum pH:
  said dehydrogenase has an optimum pH at about 8.0 to 9.0;

(4) pH stability:
  said dehydrogenase is stable at a pH of from 6.0 to 9.0;

(5) Optimum temperature:
  said dehydrogenase has an optimum temperature at about 35° C. to 45° C.

(6) Temperature stability:
  said dehydrogenase is stable up to about 40° C. by 90% or more;

(7) Measurement of activity:
  3.0 ml in total of an enzyme-containing solution comprised of 1.5 ml of 0.2M potassium phosphate buffer (pH 8.0), 0.3 ml of 0.25% by weight nitrotetrazolium blue, 0.3 ml of 2% by weight nonionic surface-active agent, 0.3 ml of an aqueous 50 mM 1,5-anhydroglucitol solution, 0.45 ml of water and 0.15 ml of an enzyme solution is reacted at 37° C., and a change in absorbance (ΔmOD/min) at 540 nm is measured; the molecular extinction coefficient of a formazan dye formed under such conditions is given as $16.7 \times 10^3$ and the quantity of the enzyme capable of forming 1 μmol of formazan in one minute is regarded as one unit, where the activity of the 1,5-anhydroglucitol dehydrogenase is determined according to the following expression:

Enzymatic activity (units/ml) =

$$\frac{\Delta mOD/\min}{16.7 \times 10^3} \times \frac{3.0}{0.15} \times \text{dilution of enzyme}$$

(8) Electron acceptor:
  besides 2,6-dichlorophenolindophenol and a ferricyanide compound, the reducing chromophoric agent is also utilizable; Coenzymes selected from the group consisting of NAD and NADP and dissolved oxygen are not utilizable;
(9) Molecular weight:
  said dehydrogenase has a molecular weight of about 55,000 as determined by dodecylsulfuric acid-polyacrylamide electrophoresis.

7. A reagent for quantitative assay for 1,5-anhydroglucitol, comprising;
  a 1,5-anhydroglucitol dehydrogenase capable of acting on 1,5-anhydroglucitol and directly catalyzing a reducing chromophoric agent in the absence of an electron carrier; and
  the reducing chromophoric agent.

8. The reagent according to claim 7, which further comprises a glucose eliminator.

9. The reagent according to claim 8, wherein said glucose eliminator contains a glucose 6-position phosphorylated enzyme and an adenosine triphosphate.

10. The reagent according to claim 7, wherein said reducing chromophoric agent is a tetrazolium compound or a salt thereof.

11. The reagent according to claim 7, wherein said 1,5-anhydroglucitol dehydrogenase is an enzyme produced by a microorganism belonging to the genus Agrobacterium and having the ability to produce the 1,5-anhydroglucitol dehydrogenase.

12. The reagent according to claim 7, wherein said 1,5-anhydroglucitol dehydrogenase is an enzyme having the following physicochemical properties:
(1) Activity:
  in the absence of electron carriers, said dehydrogenase specifically acts on 1,5-anhydroglucitol to oxidize its hydroxyl group at the 2-position and catalyzes the reaction of directly reducing the reducing chromophoric agent;
(2) Substrate specificity:
  said dehydrogenase strongly acts on 1,5-anhydroglucitol and weakly acts on L-sorbose and said dehydrogenase also slightly acts on D-glucose;
(3) Optimum pH:
  said dehydrogenase has an optimum pH at about 8.0 to 9.0;
(4) pH stability:
  said dehydrogenase is stable at a pH of from 6.0 to 9.0;
(5) Optimum temperature:
  said dehydrogenase has an optimum temperature at about 35° C. to 45° C.;
(6) Temperature stability:
  said dehydrogenase is stable up to about 40° C. by 90% or more;
(7) Measurement of activity:
  3.0 ml in total of an enzyme-containing solution comprised of 1.5 ml of 0.2M potassium phosphate buffer (pH 8.0), 0.3 ml of 0.25% by weight nitrotetrazolium blue, 0.3 ml of 2% by weight nonionic surface-active agent, 0.3 ml of an aqueous 50 mM 1,5-anhydroglucitol solution, 0.45 ml of water and 0.15 ml of an enzyme solution is reacted at 37° C., and a change in absorbance (ΔmOD/min) at 540 nm is measured; the molecular extinction coefficient of a formazan dye formed under such conditions is given as $16.7 \times 10^3$ and the quantity of the enzyme capable of forming 1 μmol of formazan in one minute is regarded as one unit, where the activity of the 1,5-anhydroglucitol dehydrogenase is determined according to the following expression:

Enzymatic activity (units/ml) =

$$\frac{\Delta mOD/\min}{16.7 \times 10^3} \times \frac{3.0}{0.15} \times \text{dilution of enzyme}$$

(8) Electron accepter:
  besides 2,6-dichlorophenolindophenol and a ferricyanide compound, the reducing chromophoric agent is also utilizable; coenzymes selected from the group consisting of NAD and NADP and dissolved oxygen are not utilizable;
(9) Molecular weight:
  said dehydrogenase has a molecular weight of about 5,000 as determined by dodecylsulfuric acid-polyacrylamide electrophoresis.

* * * * *